United States Patent [19]

Yamada et al.

[11] 4,148,688

[45] Apr. 10, 1979

[54] PROCESS FOR PREPARING L-METHIONINE

[75] Inventors: Hideaki Yamada, Kyoto; Satomi Takahashi, Takatsuki; Kazushige Sumino, Akashi; Hirotaka Fukumitsu, Kakogawa; Koji Yoneda, Amagasaki, all of Japan

[73] Assignee: Kanegafuchi Kagaku Kogyo Kabushiki Kaisha, Osaka, Japan

[21] Appl. No.: 763,710

[22] Filed: Jan. 28, 1977

[30] Foreign Application Priority Data

Feb. 4, 1976 [JP] Japan .................................. 51-11574

[51] Int. Cl.² ............................................. C12D 13/06
[52] U.S. Cl. .......................................... 195/29; 195/2
[58] Field of Search ....................................... 195/2, 29

[56] References Cited

U.S. PATENT DOCUMENTS

| 3,963,573 | 6/1976 | Stauffer | 195/29 |
| 3,964,970 | 6/1976 | Dinelli et al. | 195/2 |

OTHER PUBLICATIONS

Amino Acid and Nucleic Acid; Hiroshi Yamada; No. 19; 1969, pp. 48–56.

*Primary Examiner*—Raymond N. Jones
*Assistant Examiner*—Robert J. Warden
*Attorney, Agent, or Firm*—Armstrong, Nikaido, Marmelstein & Kubovcik

[57] ABSTRACT

A process for preparing L-methionine by subjecting DL- or L-N-carbamoylmethionine to the action of a cultured broth, cells or treated cells of microorganisms having a capability in asymmetrically hydrolyzing the carbamoyl group of N-carbamoylmethionine. The process is suited for large-scale economical manufacturing of L-methionine.

8 Claims, No Drawings

PROCESS FOR PREPARING L-METHIONINE

BACKGROUND OF THE INVENTION

The present invention relates to a novel process for preparing L-methionine from DL- or L-N-carbamoylmethionine by employing cells or treated cells of microorganisms.

In general, optically active L-amino acids are directly prepared by fermentation or prepared by optically resolving chemically synthesized DL-amino acids. No advantageous method for directly preparing L-methionine by fermentation is known, and L-methionine is prepared exclusively by subjecting chemically synthesized DL-methionine to N-acetylation and selectively hydrolyzing only L-N-acetylmethionine by employing acylase enzyme. However, such a method has the disadvantage that the cost becomes dear, since the acetylation of DL-methionine must be conducted and moreover expensive acylase must be employed. The thus prepared L-methionine is expensive and, therefore, the use thereof has been limited to medicines.

OBJECTS OF THE INVENTION

It is an object of the present invention to provide a novel process for preparing L-methionine from DL- or L-N-carbamoylmethionine by utilizing inexpensive enzymes of microorganisms.

A further object of the invention is to provide a process for economically preparing L-methionine which is suited for large-scale manufacturing.

Another object of the invention is to provide a novel method of optical resolution of DL-methionine.

These and other objects of the invention will become apparent from the description hereinafter.

DETAILED DESCRIPTION

It has now been found that the above-mentioned objects can be accomplished by subjecting DL- or L-N-carbamoylmethionine to the action of a cultured broth, cells or treated cells of microorganisms having a capability in asymmetrically hydrolyzing the carbamoyl group of N-carbamoylmethionine.

According to the present invention, optically active L-methionine can be effectively prepared from DL- or L-N-carbamoylmethionine by the catalytic action of enzymes of microorganisms, which may be represented by the following equation:

$$CH_3SCH_2CH_2\underset{NHCONH_2}{\underset{|}{CH}}COOH$$

[DL or L]

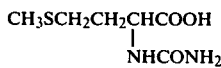

$$CH_3SCH_2CH_2\underset{NH_2}{\underset{|}{CH}}COOH$$

[L]

The expression "capability in asymmetrically hydrolyzing the carbamoyl group of N-carbamoylmethionine" as used herein means a capability to selectively hydrolyze the carbamoyl group of L-N-carbamoylmethionine.

DL-N-carbamoylmethionine, which can be synthesized by the reaction of DL-methionine with potassium cyanate, when subjected to the action of a cultured broth, cells or treated cells of microorganisms having the above-mentioned capability, is converted into only L-methionine without substantially producing D-methionine. Therefore, the process of the present invention is available as a novel method of optical resolution of DL-methionine. There has not been seen an instance of success in the production of L-methionine from N-carbamoylmethionine by utilizing enzymes of microorganisms. Although an instance of the attempt using Bacillus coagulans is known [Amino Acid and Nucleic Acid, No. 19, 48(1969)], no production of methionine is observed. Therefore, the present invention is the first invention relating to the reaction of asymmetrically hydrolyzing carbamoyl group at the N-position by utilizing enzymes of microorganisms.

The advantage of the present invention is that optically active L-methionine can be manufactured on a large scale by utilizing the process of the present invention at the final step of a method of synthesizing DL-methionine which is preferably practiced at present. For instance, in the method of synthesis of DL-methionine as expressed by the following equation, 5-(2-methylthioethyl)-hydantoin which is an important intermediate is synthesized in a form of DL-form, and it is usually hydrolyzed under alkaline conditions to produce DL-methionine.

a) $CH_3SH + CH_2=CHCHO \longrightarrow CH_3SCH_2CH_2CHO$ b) $CH_3SCH_2CH_2CHO + (NH_4)_2CO_3$

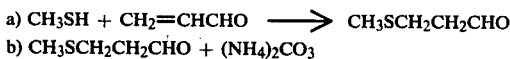

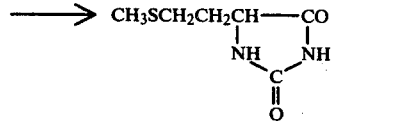

DL-5-(2-methylthioethyl)hydantoin c) 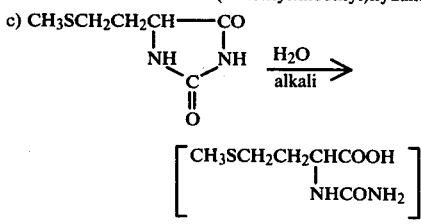

DL-N-carbamoylmethionine $$\xrightarrow[\text{alkali}]{H_2O} CH_3SCH_2CH_2\underset{NH_2}{\underset{|}{CH}}COOH + CO_2 + NH_3$$

It is well known that DL-N-carbamoylmethionine can be obtained in high yields when hydrolyzing DL-5-(2-methylthioethyl)hydantoin under mild alkaline conditions. Optically active L-methionine can be effectively synthesized by applying the optically specific, biochemical reaction of the present invention to the thus produced DL-N-carbamoylmethionine.

In the present invention DL- or L-N-carbamoylmethionine is employed as the starting material. In general, it is preferable to employ DL-N-carbamoylmethionine which may be prepared by reacting DL-methionine with potassium cyanate according to a known method or may be derived from DL-5-(2-methylthioethyl)- hydantoin obtained as an intermediate in the course of the synthesis of DL-methionine.

DL- and L-N-carbamoylmethionine may also be employed in a form of inorganic salts thereof such as the sodium salt, potassium salt and ammonium salt or organic salts thereof such as the pyridinium salt and quaternary ammonium salt, unless the reaction is inhibited. Also, N-carbamoylmethionine and salts thereof may be those containing impurities, for instance, a reaction mixture containing DL-N-carbamoylmethionine which is synthetically obtained, and they may be employed in the present invention, unless the reaction is inhibited.

The microorganisms employed in the present invention are those having a capability in asymmetrically hydrolyzing the carbamoyl group of N-carbamoylmethionine to produce L-methionine, and such microorganisms are selected by examining the presence of the above capability from wild strains present in nature, strains deposited in public organizations and microorganisms obtained by artificial mutation from these strains. As an examining method of this capability, for instance, a method as stated below may be employed: First, cells are collected by centrifuging 10 ml. of a cultured broth of a microorganism, and then washed with 10 ml. of a 0.9% by weight saline water. Again, cells are collected by centrifugation. The thus obtained intact cells (wet weight: 200 to 2,000 mg.) are added to 10 ml. of a 0.5 to 1.0% by weight aqueous solution of DL-N-carbamoylmethionine. Then, the reaction is carried out at pH 7 to 10 at a temperature of 30° to 37° C. for 40 hours. A microorganism which produces L-methionine at a conversion of not less than 1% by mole is adopted in the present invention. However, the above-mentioned reaction conditions are one instance and it should be understood that the present invention is not limited thereto.

The microorganisms employed in the present invention are those passing the above examination and are selected from bacteria, actinomycetes, molds, yeasts and deuteromycetes. Such microorganisms can be found in a very wide range of the genus from the standpoint of taxonomy. For instance, examples of the bacteria are Achromobacter, Aerobacter, Aeromonas, Agrobacterium, Alcaligenes, Arthrobacter, Bacillus, Brevibacterium, Corynebacterium, Enterobacter, Erwinia, Escherichia, Klebsiella, Microbacterium, Micrococcus, Protaminobacter, Proteus, Pseudomonas, Sarcina, Staphylococcus and Xanthomonas. Examples of the actinomycetes are Actinomyces, Mycobacterium, Nocardia and Streptomyces. Examples of the molds are species belonging to Aspergillus. Examples of the yeasts are Candida, Saccharomyces and Torulopsis.

The process of the present invention utilizes an intracellular enzyme of microorganisms, and such an enzyme can be prepared by culturing a microorganism in a conventional manner. Although the culture is usually effected in a liquid culture medium, solid surface culture may also be employed. In general, a culture medium contains carbon and nitrogen sources, inorganic salts and organic nutrients, which can be assimilated by microorganisms. It is preferable to add a small amount of DL- or L-N-carbamoylmethionine being the reaction substrate, or DL-5-(2-methylthioethyl)hydantoin to the culture medium in order to adaptively enhance the activity of the desired enzyme. The culture conditions are selected from the temperature range of 20° to 85° C. and pH range of 4 to 11 in accordance with the optimum growth conditions of the employed strain, and usually microorganisms are cultured at a temperature of 20° to 40° C. at a pH of 5 to 9 for 10 to 75 hours. During the culture, the growth of microorganism may be accelerated by aeration and agitation.

The thus cultured microorganism is employed in a form of the cultured broth, cells or treated cells in the hydrolysis reaction of N-cabamoylmethionine. The strong reaction is usually caused by employing the cultured broth containing the cells of microorganisms as it is. In cases where the components in the cultured broth are an obstacle to the reaction or it is desired to increase the amount of cells, cells separated from the cultured broth are employed. Although the objects of the invention can be sufficiently attained by employing the intact cells, the cells may be employed in a form of the dried cells, for example, lyophilized cells and acetone powder, for the convenience of the storage or handling. Also, the cells can be employed in a form of the treated cells, for example, crushed cells and cellular extract. Further, these cells and treated cells may be immobilized in a conventional manner.

The reaction substrate is usually admixed with the cultured broth, cells or treated cells in an aqueous medium to make the enzymes of microorganisms act catalytically on the substrate. The reaction may also be effected by adding the reaction substrate to a liquid culture medium during the culture of microorganisms.

The concentration of the reaction substrate, DL- or L-N-carbamoylmethionine, is selected from 0.1 to 50% by weight. The substrate, usually present in a form of the solution, may be present in a form of the suspension. The pH of the aqueous medium for the hydrolysis reaction is selected from 6 to 11, and preferably the reaction is carried out at a pH of 7 to 10. When pH is lower than 6, the reaction rate is very slow. Also, when pH is higher than 11, undesirable side reactions may occur. Since the pH of the aqueous medium rises with the progress of the hydrolysis reaction, it is suitable to maintain the optimum pH by adding a neutralizing agent to the medium at an appropriate time during the reaction. As the neutralizing agent, acids such as phosphoric acid, hydrochloric acid and sulfuric acid are employed. The hydrolysis reaction is carried out at a temperature suitable for the enzyme of the employed microorganism, and usually at a temperature of 20° to 85° C. The reaction time varies depending on the activity of the employed microorganism and the reaction temperature, and is usually selected from 10 to 100 hours.

The produced L-methionine is isolated from the reaction mixture in a conventional manner. For instance, after removing insoluble materials such as cells from the reaction mixture, L-methionine is adsorbed by passing the reaction mixture through a column of a strongly acidic cation exchange resin such as H-type, and then eluted from the resin with a dilute aqueous ammonia. The crystals of L-methionine are obtained by concentrating the eluate.

According to the present invention, only L-form of N-carbamoylmethionine is converted to L-methionine and the D-form remains in the reaction mixture without being converted. The present inventors have found the fact that optically active N-carbamoylmethionine racemizes in a strongly alkaline aqueous solution. Therefore, the residual D-N-carbamoylmethionine may be reused as the reaction substrate by converting it into the DL-form. Thus, by combining the process of the present invention with a racemization step, L-methionine can be efficiently prepared from DL-N-carbamoylmethionine, so that the industrial value of the invention is very high.

The present invention is more particularly described and explained by means of the following Examples, in which all percents are percent by weight unless otherwise stated. These examples are intended to illustrate the invention and are not to be construed to limit the scope of the invention.

EXAMPLE 1

A liquid culture medium of pH 7.0 containing the following components was prepared, and 9 ml. portions thereof were poured into 70 ml. test tubes and steam-sterilized at a temperature of 120° C. for 10 minutes.

| Medium Components | |
|---|---|
| Glucose | 0.5% |
| Yeast extract | 0.1% |
| Peptone | 0.5% |
| $KH_2PO_4$ | 0.5% |
| $MgSO_4 \cdot 7H_2O$ | 0.02% |
| $FeSO_4 \cdot 7H_2O$ | 10 p.p.m. |
| $MnSO_4 \cdot 4H_2O$ | 10 p.p.m. |

To each test tube was added 1 ml. of a 3.3% aqueous solution of DL-N-carbamoylmethionine sterilized (pH 7.0) under sterile conditions. Each microorganism shown in Table 1 was inoculated into the medium with a platinum loop, and then cultured at a temperature of 33° C. for 22 hours with shaking. Cells were separated from each cultured broth by centrifugation and washed with 5 ml. of 0.9% saline water. The thus obtained cells from each cultured broth were suspended into a mixture having the following composition.

Composition of Mixture (1) 5.0 ml. of an aqueous solution of pH 7.6 containing 2.0% of DL-N-carbamoylmethionine (substrate content: 100 mg.)

(2) 5.0 ml. of 0.2 M phosphate buffer solution of pH 7.6

Into the mixture of the above (1) and (2), the cells were suspended, and the reaction was carried out on standing at 33° C. for 40 hours. After the completion of the reaction, the reaction mixture was centrifuged and the amount of methionine in the resulting supernatant liquid was determined by a bioassay using a strain requiring L-methionine. Further, the product was subjected to a silica-gel thin-layer chromatography (solvent: n-butanol/acetic acid/water=4/1/1) to separate the methionine spot, and the amount of methionine was colorimetrically determined by developing color with ninhydrin.

The results are shown in Table 1.

Table 1

| Strain | Amount of produced L-methionine mg./ml. | Conversion % by mole |
|---|---|---|
| Achromobacter polymorph | 0.35 | 4.5 |
| Achromobacter superficialis | 0.30 | 3.9 |
| Aerobacter cloacae IAM 1221 | 0.70 | 9.0 |
| Aeromonas punctata IAM 1646 | 0.35 | 4.5 |
| Agrobacterium rhizogenes IFO 13259 | 1.45 | 18.7 |
| Alcaligenes faecalis IAM 1015 | 0.30 | 3.9 |
| Arthrobacter ureafaciens IFO 12140 | 0.10 | 1.3 |
| Bacillus circulans IFO 3329 | 0.25 | 3.2 |
| Bacillus licheniformis IFO 12195 | 0.10 | 1.3 |
| Bacillus megaterium IFO 3003 | 0.40 | 5.2 |

Table 1-continued

| Strain | Amount of produced L-methionine mg./ml. | Conversion % by mole |
|---|---|---|
| Bacillus pumilis IFO 3028 | 0.40 | 5.2 |
| Brevibacterium flavum ATCC 21129 | 0.10 | 1.3 |
| Corynebacterium sepedonicum IFO 3306 | 3.70 | 47.7 |
| Enterobacter cloacae IFO 13535 | 0.05 | 0.6 |
| Erwinia aroideae IFO 12380 | 0.10 | 1.3 |
| Escherichia coli ATCC 8739 | 0.45 | 5.8 |
| Klebsiella pneumoniae IFO 3319 | 0.20 | 2.6 |
| Microbacterium flavum ATCC 10340 | 0.17 | 2.2 |
| Micrococcus roseus IFO 3764 | 0.28 | 3.6 |
| Mycobacterium smegmatis ATCC 607 | 2.60 | 33.5 |
| Nocardia corallina IFO 3338 | 0.20 | 2.6 |
| Protaminobacter ruber IFO 3708 | 0.40 | 5.2 |
| Proteus mirabilis IFO 3849 | 0.10 | 1.3 |
| Pseudomonas aeruginosa IFO 3445 | 0.55 | 7.1 |
| Pseudomonas solanacearum IFO 12510 | 0.10 | 1.3 |
| Sarcina lutea IFO 3232 | 0.55 | 7.1 |
| Sarcina variabilis IFO 3067 | 0.40 | 5.2 |
| Staphylococcus aureus IFO 12732 | 0.10 | 1.3 |
| Xanthomonas campestris IAM 1671 | 0.45 | 5.8 |

(Note) The catalogue numbers of strains shown in Table 1 show the strains deposited in the following organization (hereinafter the same).
IAM: the Institute of Applied Microbiology, University of Tokyo (Japan)
IFO: Institute of Fermentation, Osaka (Japan)
ATCC: American Type Culture Collection (U.S.A.)

EXAMPLE 2

A liquid culture medium of pH 7.0 containing the following components was prepared, and 9 ml. portions thereof were poured into 70 ml. test tubes and steam-sterilized at 120° C. for 10 minutes.

| Medium Components | |
|---|---|
| Glucose | 2.0% |
| Soybean meal | 1.0% |
| Yeast extract | 0.25% |
| Meat extract | 0.1% |
| KCl | 0.4% |
| $(NH_4)_2SO_4$ | 0.5% |
| $KH_2PO_4$ | 0.02% |

To each test tube was added 1 ml. of a 2% aqueous solution of DL-N-carbamoylmethionine sterilized (pH 7.0) under sterile conditions. Each microorganism shown in Table 2 was inoculated into the medium with a platinum loop, and then cultured at 30° C. for 40 hours with shaking. Cells were separated from each cultured broth by centrifugation and washed with 5 ml. of 0.9% saline water. The thus obtained cells from each cultured broth were suspended into a mixture having the following composition.

Composition of Mixture (1) 5.0 ml. of an aqueous substrate solution of pH 7.6 containing 2.0% of DL-N-carbamoylmethionine (substrate content: 100 mg.)

(2) 5.0 ml. of 0.2 M phosphate buffer solution of pH 7.6

Into the mixture of the above (1) and (2), the cells were suspended, and the reaction was carried out at 33° C. for 40 hours. After the completion of the reaction, the amount of the produced L-methionine was determined in the same manner as in Example 1.

The results are shown in Table 2.

Table 2

| Strain | Amount of produced L-methionine mg./ml. | Conversion % by mole |
|---|---|---|
| *Streptomyces almquisti* ATCC 618 | 0.13 | 1.7 |
| *Streptomyces aureus* IFO 3175 | 0.42 | 5.4 |
| *Streptomyces flaveolus* IFO 3408 | 0.50 | 6.4 |
| *Actinomyces griseoruber* IFO 12872 | 0.37 | 4.8 |

EXAMPLE 3

A 2 liter shaking flask was charged with 300 ml. of a liquid culture medium of pH 7.0 containing the following components, and steam sterilization was effected at 120° C. for 15 minutes.

| Medium Components | |
|---|---|
| Glucose | 1.0% |
| Peptone | 0.5% |
| Meat extract | 0.2% |
| Yeast extract | 0.5% |
| KH$_2$PO$_4$ | 0.1% |
| MgSO$_4$ . 7H$_2$O | 0.04% |
| FeSO$_4$ . 7H$_2$O | 3 p.p.m. |
| MnSO$_4$ . 4H$_2$O | 3 p.p.m. |

After adding sterilized DL-N-carbamoylmethionine to the liquid culture medium in an amount of 0.3%, 10 ml. of a cell suspension of Corynebacterium sepedonicum IFO 3306 which was previously cultured in the same culture medium as above was inoculated into the culture medium and then the culture was carried out at 33° C. for 22 hours with shaking. Cells were separated from the resulting cultured broth by centrifugation and washed with 100 ml. of a 0.9% saline water. Then, 50 ml. of a 0.9% saline water was added to cells to prepare a cell suspension.

A sterilized 500 ml. ground stopper Erlenmeyer flask was charged with a mixture having the following composition, and the reaction was carried out on standing at 33° C. for 2 days.

Composition of Mixture (1) 50 ml. of an aqueous substrate solution of pH 7.6 containing 3.0% of DL-N-carbamoylmethionine (2) 50 ml. of 0.2 M phosphate buffer solution of pH 7.6 (further containing 6 p.p.m. of FeSO$_4$·7H$_2$O and 6 p.p.m. of MnSO$_4$·4H$_2$O)

(3) 50 ml. of the above cell suspension

After the completion of the reaction, it was confirmed that methionine was produced in the reaction mixture in an amount of 3.85 mg./ml. The conversion was 49.6% by mole.

After removing cells from the reaction mixture by centrifugation, methionine was adsorbed by passing the resulting supernatant liquid through a column of a strongly acidic cation exchange resin of H-type, and the eluted from the resin with a dilute aqueous ammonia. The eluate was concentrated under reduced pressure to give 480 mg. of crystalline methionine. The specific rotatory power of the thus isolated methionine was $[\alpha]_D^{25} = +22.0°$ (c=1, 5 N-HCl), and that of an authentic L-methionine was $[\alpha]_D^{25} = +22.5°$. Also, Rf value by paper chromatography using a mixture of two solvents as a developing solvent, value of elementary analysis and infrared spectrum of the isolated methionine agreed with those of authentic L-methionine. The reaction product was identified as optically active L-methionine.

Further, reaction products obtained by employing other microorganisms listed in Table 1 or 2, for instance, Aerobacter cloacae IAM 1221, Agrobacterium rhizogenes IFO 13259, Xanthomonas campestris IAM 1671, Pseudomonas aeruginosa IFO 3445, Sarcina lutea IFO 3232, Escherichia coli ATCC 8739, Bacillus pumilus IFO 3028 and Streptomyces flaveolus IFO 3408 are also identified as L-methionine in the same manner as above.

EXAMPLE 4

A 50 ml. aqueous cell suspension of Corynebacterium sepedonicum IFO 3306 was prepared in the same manner as in Example 3. Then, two kinds of mixtures having the following composition were prepared and the hydrolysis reaction was carried out in the same manner as in Example 3, respectively.

Composition of Mixture A (1) 25 ml. of an aqueous substrate solution of pH 7.6 containing 3.0% of L-N-carbamoylmethionine (2) 25 ml. of 0.2 M phosphate buffer solution of pH 7.6 (further containing 6 p.p.m. of FeSO$_4$·7H$_2$O and 6 p.p.m. of MnSO$_4$·4H$_2$O)

(3) 25 ml. of the above cell suspension

Composition of Mixture B

The composition of the mixture B was the same as that of the mixture A except that the component (1) of the mixture A was replaced with 25 ml. of aqueous substrate solution of pH 7.6 containing 3.0% of D-N-carbamoylmethionine These mixtures were placed in a sterilized 200 ml. ground stopper Erlenmeyer flask for the hydrolysis reaction, respectively.

After the completion of the reaction, the amount of the produced L-methionine was determined. It was observed that L-methionine was produced in the reaction mixture A in an amount of 3.30 mg./ml. but neither D- nor L-methionine was produced in the reaction mixture B.

EXAMPLE 5

A 50 ml. aqueous cell suspension of Corynebacterium sepedonicum IFO 3306 was prepared in the same manner as in Example 3. Also, 0.2 M phosphate buffer solutions of pH 5.0, 5.5, 5.8, 6.1, 6.6, 7.2, 7.8 and 8.4 and Na$_2$CO$_3$-NaHCO$_3$ buffer solutions of pH 9.0, 9.5, 10.0 and 10.7 were prepared. Then, mixtures having the following composition were prepared and placed in test tubes, respectively. The hydrolysis reaction was carried out at 33° C. for 44 hours.

Composition of Mixture (1) 2.0 ml. of the above buffer solution (2) 2.0 ml. of an aqueous substrate solution containing 3.0% of L-N-carbamoylmethionine which was adjusted to the same pH as that of the buffer solution (3) 2.0 ml. of the above cell suspension After the completion of the reaction, the amount of the produced methionine was determined by a bioassay and colorimetric determinations in the same manner as in Example 1.

The results are shown in Table 3. As a result, it was confirmed that the optimum pH of the hydrolysis reaction of L-N-carbamoylmethionine using Corynebacterium sepedonicum IFO 3306 was within the range of 7 to 8.5.

Table 3

| pH | | L-methionine | |
|---|---|---|---|
| At the beginning of reaction | At the end of the reaction | Amount of produced L-methionine mg./ml. | Conversion % by mole |
| 5.0 | 5.4 | ± | <1 |
| 5.5 | 5.9 | ± | <1 |
| 5.8 | 6.0 | ± | <1 |
| 6.1 | 6.4 | ± | <1 |
| 6.6 | 6.9 | 1.0 | 13 |
| 7.2 | 7.5 | 3.2 | 41 |
| 7.8 | 8.1 | 3.5 | 45 |
| 8.4 | 8.7 | 3.8 | 49 |
| 9.0 | 9.6 | 2.3 | 30 |
| 9.5 | 9.7 | 2.2 | 28 |
| 10.0 | 9.8 | 1.8 | 23 |
| 10.7 | 9.9 | 1.1 | 14 |

EXAMPLE 6

A liquid culture medium of pH 7.6 containing the following components was prepared, and 9 ml. portions thereof were poured into test tubes and were steam-sterilized at 120° C. for 10 minutes.

| Medium Components | |
|---|---|
| Sucrose | 10.0% |
| Yeast extract | 0.2% |
| (NH$_4$)$_2$HPO$_4$ | 0.2% |
| KH$_2$PO$_4$ | 0.1% |
| MgSO$_4$ . 7H$_2$O | 0.1% |
| CaCo$_3$ | 0.2% |

To each test tube was added 1 ml. of a 3.0% aqueous solution of sterilized DL-N-carbamoylmethionine (pH 7.0) under sterile conditions. Each microorganism shown in Table 4 from a storage slant was inoculated with a platinum loop, and cultured at 30° C. for 40 hours with shaking. Then, by employing cells separated from each cultured broth in the same manner as in Example 1, the hydrolysis reactions of DL-N-carbamoylmethionine were carried out under the same conditions as in Example 1.

After the completion of the reaction, the amount of the produced L-methionine was determined in the same manner as in Example 1.

The results are shown in Table 4.

Table 4

| Strain | Amount of produced L-methionine mg./ml. | Conversion % by mole |
|---|---|---|
| Candida intermedia IFO 0761 | 0.20 | 2.6 |
| Saccharomyces cerevisiae IFO 0971 | 0.10 | 1.3 |
| Torulopsis famata IFO 0728 | 0.10 | 1.3 |

EXAMPLE 7

A liquid culture medium of pH 6.0 containing the following components was prepared, and placed in a test tube in an amount of 9 ml. and steam-sterilized at 120° C. for 10 minutes.

| Medium Components | |
|---|---|
| Glucose | 10.0% |
| Peptone | 0.2% |
| KNO$_3$ | 0.2% |
| (NH$_4$)H$_2$PO$_4$ | 1.0% |
| MgSO$_4$ . 7H$_2$O | 0.05% |
| CaCl$_2$ | 0.01% |

A sterilized aqueous solution of pH 7.0 containing 3.0% of DL-N-carbamoylmethionine was added to the test tube under sterile conditions, and Aspergillus nigar IAM 3007 was inoculated with a platinum loop. The culture was carried out at 26° C. for 40 hours with shaking. By employing cells separated from the resulting cultured broth in the same manner as in Example 1, the hydrolysis reaction of DL-N-carbamoylmethionine and the determination of the produced L-methionine were carried out in the same manner as in Example 1.

The amount of the produced L-methionine was 0.10 mg./ml. and the conversion was 1.3% by mole.

What we claim is:

1. A process for preparing L-methionine which comprises subjecting DL- or L-N-carbamoylmethionine to the action of an enzyme which is in the form of a cultured broth containing a microorganism or separated cells of said microorganism in an aqueous medium, said enzyme being capable of hydrolyzing the carbamoyl group of L-N-carbamoylmethionine so as to substantially produce only L-methionine, and recovering said L-methionine from the medium.

2. The process of claim 1, wherein said separated cells are intact cells or dried cells.

3. The process of claim 1, wherein said separated cells are crushed cells or cellular extract.

4. The process of claim 1, wherein said separated cells are immobilized.

5. The process of claim 1, wherein the process is conducted in an aqueous medium of pH 6 to 11.

6. The process of claim 1, wherein said microorganism is a member selected from the group consisting of Achromobacter, Aerobacter, Aeromonas, Agrobacerium, Alcaligenes, Arthrobacter, Bacillus, Brevibacterium, Corynebacterium, Enterobacter, Erwinia, Escherichia, Klebsiella, Microbacterium, Micrococcus, Protaminobacter, Proteus, Pseudomonas, Sarcina, Staphylococcus, Xanthomonas, Actinomyces, Mycobacterium, Nocardia, Streptomyces, Aspergillus, Candida, Saccharomyces and Torulopsis.

7. The process of claim 1, wherein said DL-N-carbamoylmethionine is subjected to the action of an enzyme which is in the form of a cultured broth containing a microorganism or separated cells of said microorganism in an aqueous medium of pH 7 to 10, said microorganism being selected from the group consisting of Corynebacterium, Mycobacterium and Agrobacterium.

8. The process of claim 1, wherein said microorganism is those cultured in a culture medium containing at least one member selected from DL-N-carbamoylmethionine, L-N-carbamoylmethionine and DL-5-(2-methylthioethyl)hydantoin which enhances the capability of the microorganism in asymmetrically hyrolyzing the carbamoyl group of N-carbamoylmethionine.

* * * * *